United States Patent
Schmidt et al.

(10) Patent No.: US 11,193,156 B2
(45) Date of Patent: *Dec. 7, 2021

(54) RECOMBINANT GLYCOPROTEINS WITH REDUCED ANTENNARY FUCOSYLATION

(71) Applicant: Cevec Pharmaceutical GmbH, Cologne (DE)

(72) Inventors: Hanns-Martin Schmidt, Cologne (DE); Markus Ribbert, Biberach an der Riss (DE); Gudrun Schiedner, Cologne (DE); Silke Wissing, Cologne (DE); Jens Wölfel, Langenfeld (DE)

(73) Assignee: Cevec Pharmaceutical GmbH, Cologne (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/496,113

(22) PCT Filed: Mar. 15, 2018

(86) PCT No.: PCT/EP2018/056502
§ 371 (c)(1),
(2) Date: Sep. 20, 2019

(87) PCT Pub. No.: WO2018/177758
PCT Pub. Date: Oct. 4, 2018

(65) Prior Publication Data
US 2020/0032311 A1 Jan. 30, 2020

(30) Foreign Application Priority Data
Mar. 29, 2017 (EP) .................................... 17000521

(51) Int. Cl.
| | | |
|---|---|---|
| *C12N 5/16* | (2006.01) | |
| *C12P 21/00* | (2006.01) | |
| *C07K 14/81* | (2006.01) | |
| *C12N 9/10* | (2006.01) | |

(52) U.S. Cl.
CPC ........ *C12P 21/005* (2013.01); *C07K 14/8125* (2013.01); *C12N 5/16* (2013.01); *C12N 9/1081* (2013.01); *C12Y 204/99001* (2013.01); *C12Y 204/99004* (2013.01)

(58) Field of Classification Search
CPC ... C12P 21/005; C12N 9/1081; C12Y 204/99; C12Y 204/99001; C12Y 204/99004
See application file for complete search history.

(56) References Cited

U.S. PATENT DOCUMENTS

| | | | |
|---|---|---|---|
| 5,262,308 | A | 11/1993 | Renato |
| 10,081,798 | B2 | 9/2018 | Wissing et al. |
| 2010/0028951 | A1 | 2/2010 | Hamilton |
| 2012/0322738 | A1 | 12/2012 | Behrens |
| 2013/0040897 | A1 | 2/2013 | Markus |
| 2017/0020992 | A1 | 1/2017 | Bolt |

FOREIGN PATENT DOCUMENTS

| | | |
|---|---|---|
| CN | 101 613 678 A | 12/2009 |
| JP | 2011519359 | 7/2011 |
| JP | 2012516690 | 7/2012 |
| JP | 2013519636 | 5/2013 |
| RU | 2479629 | 4/2011 |
| WO | WO 2008/077547 | 7/2008 |
| WO | WO 2009/127826 | 10/2009 |
| WO | WO 2010/094280 | 8/2010 |
| WO | WO 2010/127939 | 11/2010 |
| WO | WO2011/101267 | 8/2011 |
| WO | WO 2011/109600 | 9/2011 |
| WO | WO 2012/077128 | 6/2012 |
| WO | WO 2013/093760 | 6/2013 |
| WO | WO 2014/015227 | 1/2014 |
| WO | WO 2014/140927 | 9/2014 |
| WO | WO 2015/134488 | 9/2015 |

OTHER PUBLICATIONS

Li et al. 2009; Cell surface sialylation and fucosylation are regulated by the cell recognition molecule L1 and PLC-gamma and cooperate to modulate embryonic stem cell survival and proliferation. FEBS Letters. 583: 700-710.*
Wissing, S. et al, Expression of glycoproteins with excellent glycosylation profile and serum half-life in CAP-Go cells, 2015, BMC Proceed. vol. 9, p. 12.
Schniedner et al, Efficient and reproducible generation of high-expressing, stable human cell lines without need for antibiotic . . . , 2008, BMC Biotechnol. vol. 8, pp. 13-23.
Kono et al, Mouse beta-galactoside alpha-2,3-sialyltransferases: comparison of in vitro substrate . . . , 1997, Glycobiology, Oxford University Press, vol. 7, pp. 469-479.
Lee et al., N-glycan analysis of human alpha1-antitrypsin produced in Chinese hamster ovary cells, 2013, Gycoconjug J vol. 30, pp. 527-547.
Lusch et al., Development and analysis of alpha1-antitrypsin neoglycoproteins: the impact of additional N-glycosylation . . . , 2013, Molc Pharmaceut vol. 10, pp. 2616-2629.
Niimi et al., High expression of N-acetylglucosaminyltransferase IVa promotes invasion of choriocarcinoma, 2012, Brit J Cancer vol. 107, pp. 1969-1977.
Priatel et al, The ST3Gal-1 Sialyltransferase controls CD8+ T-Lymphocyte homeostasis by modulating O-glycan biosynthesis, 2000, Immunity vol. 12, pp. 273-283.
Shang et al, Molecular cloning and expression of Galb1,3GalNAc a2,3-sialyltransferase from human fetal liver, 1999, Eur. J. Biochem. vol. 265, pp. 580-588.
Thim et al., Purification and characterization of a new recombinant factor VIII (N8), 2010, Haemophilia vol. 16, pp. 349-359.
Vallejo-Ruiz et al, Delineation of the minimal catalytic domain of human Galbetal-3GalNAc-alpha-2,3-sialyltransferase, 2001, Biochim Biophys Acta vol. 1549, pp. 161-173.

(Continued)

*Primary Examiner* — Karen Cochrane Carlson
(74) *Attorney, Agent, or Firm* — HelixIP LLP

(57) ABSTRACT

The present invention relates to methods for reducing antennary fucosylation of complex N-glycans in recombinantly expressed glycoproteins, cell lines that can be used in said methods, respective recombinant glycoproteins, and methods for expressing the same in said cell lines.

15 Claims, 10 Drawing Sheets

Figure 1:
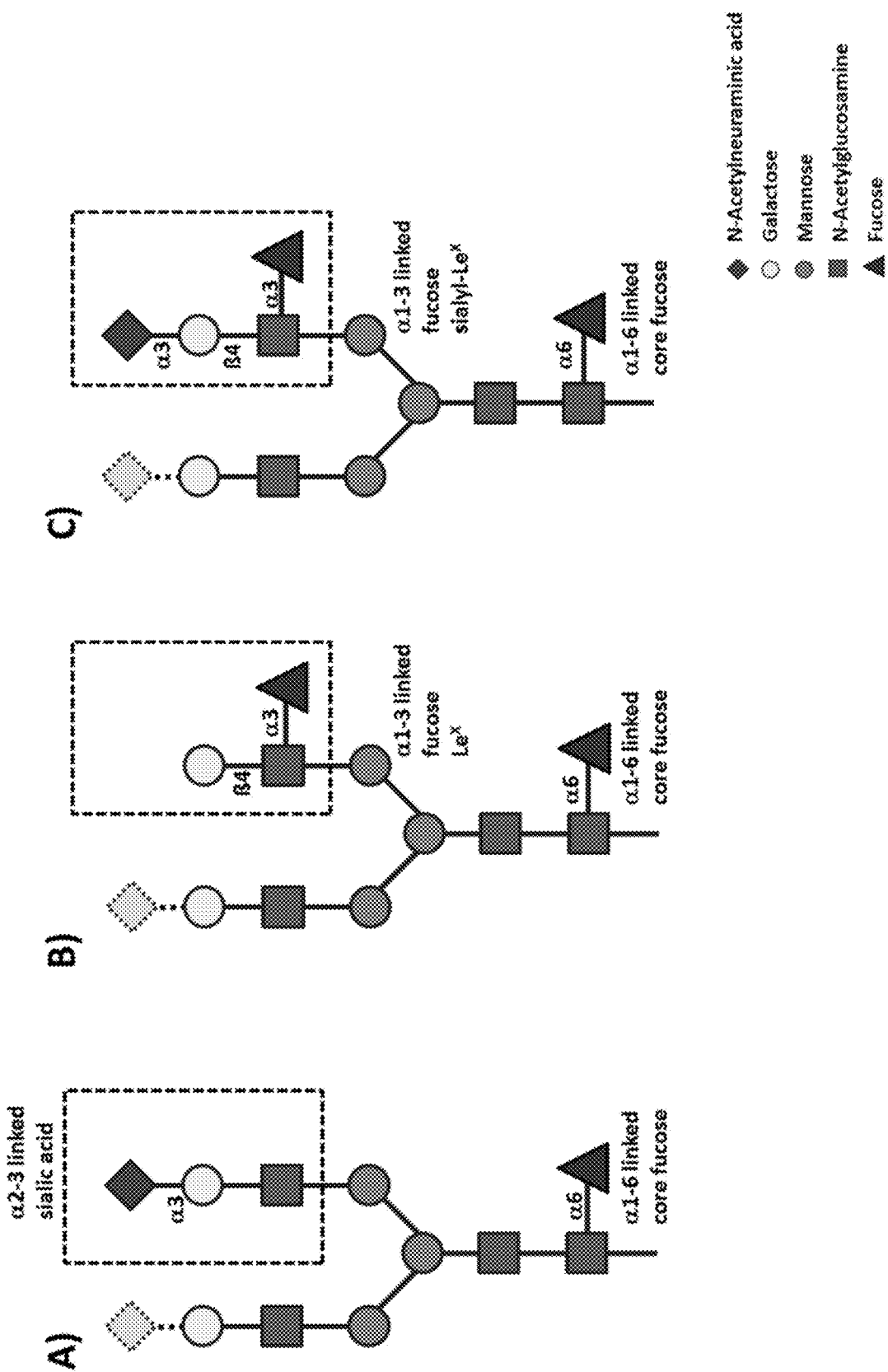

Specification includes a Sequence Listing.

(56) References Cited

OTHER PUBLICATIONS

Wang et al., Structural characterization of recombinant alpha1-antitrypsin expressed in a human cell line, Analy Biochem vol. 437, pp. 20-28.
Whitehouse et al., A transfected sialyltransferase that is elevated in bresat cancer and localizes to the medial/trans-Golgi . . . , 1997, J. Cell Biol. vol. 137, pp. 1229-1241.
Backstrom et al., Recombinant MUC1 mucin with a breast cancer like O-glycosylation produced in large amounts in CHO cell, 2003, Biochem. J. vol. 376, pp. 677-686.
Blanchard et al., N-glycosylation and biological activity of recombinant human alpha-antitrypsin expressed . . . , 2011, Biotechnol Bioengin vol. 108, pp. 2118-2128.
Blixt et al, Efficient chemoenzymatic synthesis of O-linked sialyl oligosaccharides, 2002, J. Am. Chem. Soc. vol. 124, pp. 5739-5746.
Castilho et al., N-glycosylation engineering of plants for the biosynthesis of glycoproteins with bisected and branched . . . , 2011, Gycobiology vol. 21, pp. 813-823.
Cheung et al., Metabolic homeostasis and tissue renewal are dependent on 1,6GlcNAc-branched N-glycans, 2007, Glycobiology vol. 17, pp. 828-837.
Dalziel et al., The relative activities of the C2GnT1 and ST3Gal-1 glycosyltransferases determine the O-Glycan tumor . . . , 2000, J. Biol. Chem. vol. 276, pp. 11007-11015.
Fukuta et al., Genetic engineering of CHO cells producing human interferon-g by transfection of sialyltransferases, 2000, Glycoconjug. J. vol. 17, pp. 895-904.

Guo et al., Effect of N-acetylglucosaminyltransferase V on the expression of other glycosyltransferases, 2004, FEBS Lett vol. 562, pp. 93-98.
Kojima et al, Kinetic properties and acceptor substrate preferences of two kinds of GalP1, 3GalNAc cu-2,3-sialyltransferase . . . , 1994, Biochemistry vol. 33, pp. 5772-5776.
Yin et al., Glycoengineering of Chinese hamster ovary cells for enhanced erythropoietin N-glycan branching and sialylation, Biotechnol Bioengin vol. 112, pp. 2343-2351.
Zhang et al, Relations of the type and branch of surface N-glycans to cell adnesion, migration and integrin expression, 2004, Molc Cell Biochem vol. 260, pp. 137-146.
Chejanovsky et al, Mutagenesis of an AUG codon in the adeno-associated virus rep gene, effects on viral DNA replication, 1989, Virol. vol. 173, pp. 120-128.
NIIMI et al, High expression of N-acetylglucosaminetransferase IVa promotes invasion of choriocarcinoma, 2012, Brit. J. Cancer vol. 107, pp. 1969-1977.
Zhang et al, Relations of the type and branch of surface N-glycans to cell adhesion, migration, and integrin expression, 2004, Molc Cell Biol vol. 260, pp. 137-146.
U.S. Appl. No. 16/077,425, filed Aug. 10, 2018. Cell Line for Producing Recombinant Glycoproteins with Di-Antennary N-Glycans, Methods Using the Same, and Recombinant Glycoproteins.
U.S. Appl. No. 16/107,009, filed Aug. 21, 2018. O-Glycan Sialylated Recombinant Glycoproteins and Cell Lines for Producing the Same.

* cited by examiner

RECOMBINANT GLYCOPROTEINS WITH REDUCED ANTENNARY FUCOSYLATION

The present invention relates to methods for reducing antennary fucosylation of complex N-glycans in recombinantly expressed glycoproteins, cell lines that can be used in said methods, respective recombinant glycoproteins, and methods for expressing the same in said cell lines.

Most current recombinant therapeutic proteins are glycoproteins. They have sugar residues attached to the amino-group of an asparagine (N-linked glycans) or the hydroxyl-group of a serine or threonine (O-linked glycans). The structure of the glycans is highly variable, depending on the specific protein and the host cell used for recombinant expression.

A very common structure of N-glycans found on glycoproteins expressed with mammalian expression platforms are so-called complex N-glycans, characterized by the core sugar sequence Manα1-6(Manα1-3)Manβ1-4GlcNAcβ1-4GlcNAcβ1-Asn-. This core structure is extended by "antennae" which are initiated by N-acetylglucosamine (GlcNAc). Typically, complex type N-glycans have two, three, or four antennae, but in rare cases five or six antennae can be found. A typical structure of a di-antennary complex type N-glycan is depicted in FIG. 1A.

Complex N-glycans can be fucosylated. In mammalian cells, fucose is either linked to the proximal GlcNAc by α1-6 linkage (core fucose) or to a distal GlcNAc on one or several of the antennae by α1-3 linkage (antennary fucose; also called Lewis$^x$ antigen (Le$^x$), CD15, or SSEA-1), displayed in FIG. 1B. If the Lewis$^x$ structure (Gal(ß-4)[Fuc(α)]GlcNAc-R) harbors an additional sialic acid, the resulting structure is called sialyl-Lewis$^x$, sialyl-Le$^x$, or SLe$^x$ (NeuAc(α1->4)Gal(ß-4)[Fuc(α1->3)]GlcNAc-R), displayed in FIG. 1C. Sialyl Lewis$^x$ structures emerge by the fucosylation of sialylated complex type N-glycans at the distal GlcNAc catalyzed by various fucosyltransferases. The role of core α1-6 fucosylation has been extensively studied for antibodies. Antibodies of the IgG class typically carry an N-glycan in the CH2 domain of the Fc region. The presence of a core fucose on these N-glycans significantly reduces the ADCC (antibody dependent cellular cytotoxicity) response mediated by the antibody in vivo. Since ADCC is usually a highly desired effect of a therapeutic antibody, several approaches are being taken to reduce the presence of core-fucose on IgGs. The highly immunogenic core α1-3 linked fucose structure only exists in plants and in invertebrates and is absent in human cells.

On immunoglobulins, typically no antennary fucose is found, however Lewis$^x$ or sialyl-Lewis$^x$ structures are easily detected on other serum-glycoproteins. Up to date little is known about its physiological role. There is evidence that antennary fucose might increase targeting to sites of inflammation via selectin interactions, but apart from that relatively little is known about the physiological role of antennary fucosylation.

When plasma proteins are recombinantly expressed, the product often shows an elevated level of antennary fucose as compared to the naturally occurring counterpart in the plasma. In order to reduce potential immunogenic effects of recombinant proteins used in replacement therapy, it is desirable that they are as similar to the endogenous protein as possible. A reduction of antennary fucose on recombinant therapeutic proteins is an important step towards this goal.

Accordingly, the technical problem underlying the present invention is to provide means for reducing antennary fucosylation (Le$^x$ or SLe$^x$) of complex N-glycans in recombinantly expressed glycoproteins, as well as respective recombinant glycoproteins and means for producing the same.

The solution to the above technical problem is achieved by the embodiments characterized in the claims.

In particular, in a first aspect, the present invention relates to a method for reducing antennary fucosylation of complex N-glycans, either Le$^x$ or sialyl-Le$^x$ in a recombinantly expressed glycoprotein, comprising the step of overexpressing together with the glycoprotein β-galactoside α-2,6-sialyltransferase 1 (ST6Gal1) and/or α-2,3-sialyltransferase 4 (ST3Gal4).

As used herein, the term "complex N-glycans" relates to N-glycans that are characterized by the core sugar sequence Manα1-6(Manα1-3)Manβ1-4GlcNAcβ1-4GlcNAcβ1-Asn-. This complex N-glycan core sugar sequence can be extended by 2 to 6 antennae which are initiated by N-acetylglucosamine (GlcNAc), wherein two, three or four antennae are typical. Said antennae are sometimes referred to herein as "complex N-glycan antennae". Further, as used herein, the term "antennary fucosylation of complex N-glycans" refers to α1-3 linkage of fucose to a distal GlcNAc on at least one of the complex N-glycan antennae. In this context, the term "distal GlcNAc" refers to any GlcNAc present in an antenna other than the glycan's initial GlcNAcs.

The term "reducing antennary fucosylation of complex N-glycans" relates to the fact that according to the present invention, by way of overexpressing ST6Gal1 and/or ST3Gal4 together with the glycoprotein, recombinant glycoprotein is generated that has a lower amount of fucosylated complex N-glycan antennae as compared to a conventional recombinant glycoprotein. Preferably, such recombinant glycoprotein is characterized by a significantly reduced antennary fucosylation of complex N-glycans as compared to the same recombinant glycoprotein expressed without overexpression of ST6Gal1 and/or ST3Gal4.

In particularly preferred embodiments, at least 80%, more preferably at least 90%, and most preferably at least 95%, or more, of the complex N-glycan antennae of the recombinantly expressed glycoprotein are not fucosylated.

The glycoprotein to be subject to the methods of the present invention is not particularly limited, provided that it is a glycoprotein having complex N-glycans and respective complex N-glycan antennae. In preferred embodiments, the glycoprotein is selected from the group consisting of α1-antitrypsin (AAT), hepatocyte growth factor (HGF), Factor VII (FVII), Factor VIII (FVIII), Factor IX (FIX), von Willebrand-Factor (vWF), alkaline phosphatase, and C1 esterase inhibitor (C1-inhibitor; C1 Inh). Further, the glycoprotein is preferably a mammalian, more preferably a human glycoprotein.

As used herein, the term "recombinantly expressed glycoprotein" relates to glycoproteins that are biotechnologically produced in genetically modified organisms or cells.

Methods for recombinantly expressing glycoproteins, as well as for overexpressing ST6Gal1 and/or ST3Gal4 together with such glycoproteins, are not particularly limited and are known in the art. Further details in this respect are provided hereinafter for the second aspect of the present invention, relating to the cell lines of the present invention.

In specific embodiments of the present invention, both ST6Gal1 and ST3Gal4 are overexpressed together with the recombinant glycoprotein.

In further specific embodiments of the present invention, (i) β-galactoside α-2,3-sialyltransferase 1 (ST3Gal1) is not overexpressed together with the recombinant glycoprotein, and/or (ii) the expression of α-1,3-mannosyl-glycoprotein 4-β-N-acetylglucosaminyltransferase A (GnTIVa), α-1,3- mannosyl-glycoprotein 4-β-N-acetylglucosaminyltransferase B (GnTIVb), and α-1,6-mannosylglycoprotein 6-β-N-acetylglucosaminyltransferase A (GnTV) is not reduced.

In this context, the term "ST3Gal1 is not overexpressed together with the recombinant glycoprotein" relates to the fact that ST3Gal1 expression is not increased in any manner as compared to native ST3Gal1 expression. In particular embodiments, ST3Gal1 is not expressed at all. Further, the term "expression of GnTIVa, GnTIVb, and GnTV is not reduced" relates to the fact that expression of said proteins is not decreased in any manner as compared to native expression of said proteins.

In a second aspect, the present invention relates to a cell line, preferably an insect, avian, or mammalian cell line, more preferably a mammalian, in particular human, cell line, that is genetically modified to overexpress β-galactoside α-2,6-sialyltransferase 1 (ST6Gal1) and/or α-2,3-sialyltransferase 4 (ST3Gal4).

As used herein, the term "cell line that is genetically modified to overexpress ST6Gal1 and/or ST3Gal4" indicates that upon genetic modification, the individual cells of the cell line display a higher expression of the respective sialyltransferase(s) than they did before the genetic modification.

Genetic modifications that allow the overexpression of a given protein are not particularly limited and are known in the art. In a particular example, the cell line comprises endogenous gene(s) encoding ST6Gal1 and/or ST3Gal4, such as e.g. human cell lines. In such cases, the cells can be genetically modified by inserting a promoter, enhancing element, and/or stabilizing element into the genome of the cells in a position suitable to cause overexpression of said nucleic acid. This can be done by homologous recombination using TALENS, Zn-finger proteins, CRISPR-CAS9, or other methods known in the art. Thus, in preferred embodiments, the cell line comprises endogenous gene(s) encoding ST6Gal1 and/or ST3Gal4, and further has at least one genetic element, selected from the group consisting of a promoter, an enhancing element, and a stabilizing element inserted into the genome in one or more position(s) suitable to cause overexpression of ST6Gal1 and/or ST3Gal4. Suitable promoters, enhancing elements and stabilizing elements are not particularly limited and are known in the art. For example, promoters include constitutive promoters, e.g. a CMV, EF1alpha, SV40, RSV, UbC, CAG, BOS or PGK promoter, and inducible promoters, e.g. tetracycline inducible promoters or other inducible promoters known in the art. Further, enhancing elements (enhancers) include CMV enhancer, ß-globin enhancer, immunoglobulin enhancer, and PGK-enhancer. Furthermore, stabilizing elements (chromatin elements) include matrix attachment regions (MARS), locus control regions (LCRs), and ubiquitously acting chromatin opening elements (UCOEs).

Alternatively, in cases where the cells do not comprise endogenous gene(s) encoding ST6Gal1 and/or ST3Gal4, or additionally, in cases where the cells do comprise endogenous gene(s) encoding ST6Gal1 and/or ST3Gal4, genetic modification of the cells can be achieved by introducing nucleic acid(s), encoding ST6Gal1 and/or ST3Gal4 into the cells. Methods for introducing nucleic acids into cells are not particularly limited and are known in the art. For example, said nucleic acids could be introduced in circular or linearized form into the cells by electroporation, nucleofection, microinjection, via viral vectors, e.g. lentiviral vectors, reagent based methods, e.g. lipids, calcium phosphate, cationic polymers or other methods known in the art. The nucleic acids can be transiently or stably introduced into the cell by episomal systems or by stable integration of the nucleic acid into the genome. Said nucleic acids can be present in the cells in the form of one or more expression vector(s), e.g. pcDNA, pCEP, pLenti, pEntr, pDest, pEF, pEAK, pCMV, pStbl, or other expression vectors known in the art. Expression of ST6Gal1 and/or ST3Gal4 can be under the control of a constitutive promoter, e.g. a CMV, EF1alpha, SV40, RSV, UbC, CAG, BOS or PGK promoter, the endogenous promoter, or of an inducible promoter, e.g. tetracycline inducible promoter or other inducible promoters known in the art. Further, the nucleic acids encoding ST6Gal1 and/or ST3Gal4 can be present as one continuous nucleic acid, or can be present as separate nucleic acids, e.g. as separate expression vectors. Said nucleic acids can contain, in addition to the coding region and a promoter, suitable restriction sites, Kozak sequences, ribosomal binding sites, chromatin modulating elements, selection cassettes, episomal replication systems, e.g. Epstein-Barr Nuclear Antigen and ori P, or SV40 ori and SV40 T-large antigen, internal ribosomal entry sites (IRES), splicing signals, and polyadenylation signals known in the art. Thus, in preferred embodiments, the cell line comprises exogenous nucleic acid(s) encoding ST6Gal1 and/or ST3Gal4.

Suitable genes encoding ST6Gal1 and/or ST3Gal4 for transfection of cell lines are not particularly limited and include any genes from any origin that encode proteins having ST6Gal1 or ST3Gal4 activity. Preferably, such genes are mammalian, more preferably human, ST6Gal1 and ST3Gal4 genes.

The cell lines according to the present invention can be derived from cell lines, e.g. mammalian cell lines, known in the art. In preferred embodiments, a cell line of the present invention can be derived from Muscovy Duck cells (AGE.CR®) African green monkey kidney epithelial cells (Vero), Madin Darby canine kidney cells (MDCK), baby hamster kidney cells (BHK), Chinese hamster ovary (CHO) cells, human hepatocarcinoma cell lines (HepG2, Huh7), human embryonic kidney 293 (HEK293) cells, human neuronal precursor cells (AGE1.HN® and NC5T11), human embryonic retinoblasts (Per.C6), myeloma cell lines (HMCLs, MM.1, U266, RPMI8226), CML tumor cell lines (NM, NM-F9), hybrid HEK293 and lymphoma cell (HKB11), or human amniocytes (CAP; cf. EP 1 230 354 B1), wherein CHO cells, HEK293 cells and CAP cells are preferred, and CAP cells are particularly preferred.

In this context, CAP cells are permanent amniocytic cell lines comprising a nucleic acid encoding the gene products of the adenovirus, in particular adenovirus type 5 (Ad5), E1A and E1B regions. CAP cells are derived from primary human amniocytes that are transformed with a nucleic acid encoding Ad5 E1A and E1B.

Accordingly, in a preferred embodiment, the cell lines according to the present invention can be derived from human primary amniocytes comprising at least one nucleic acid encoding the gene products of the adenoviral E1 and pIX region, preferably E1 and pIX region of adenovirus type 5 (Ad5) from nt. 505 to 4079, in which E1A is under the control of the murine phosphoglycerate kinase (pgk) promoter, while E1B and pIX expression is controlled from their natural promoters. The E1B downstream intron, splice acceptor and polyA signal are replaced by corresponding motifs from SV40.

In specific embodiments of the present invention, the cell line of the present invention is genetically modified to overexpress both ST6Gal1 and ST3Gal4.

In further specific embodiments of the present invention, the cell line of the present invention is not genetically modified to (i) overexpress β-galactoside α-2,3-sialyltransferase 1 (ST3Gal1), and/or (ii) reduce the expression of α-1,3-mannosyl-glycoprotein 4-β-N-acetylglucosaminyltransferase A (GnTIVa), α-1,3-mannosyl-glycoprotein 4-β-N-acetylglucosaminyltransferase B (GnTIVb), and α-1,6-mannosylglycoprotein 6-β-N-acetylglucosaminyltransferase A (GnTV).

In this context, the term "the cell line is not genetically modified to overexpress ST3Gal1" relates to the fact that ST3Gal1 expression is not increased in any manner as compared to the cell line's native ST3Gal1 expression. In particular embodiments, ST3Gal1 is not expressed at all. Further, the term "the cell line is not genetically modified to reduce the expression of GnTIVa, GnTIVb, and GnTV" relates to the fact that expression of said proteins is not decreased in any manner as compared to native expression of said proteins in the cell line.

The cell lines according to this second aspect of the present invention are capable of reducing antennary fucosylation of complex N-glycans in recombinant glycoproteins expressed in said cell lines.

In a third aspect, the present invention relates to a recombinant glycoprotein having complex N-glycans, wherein antennary fucosylation of the complex N-glycans is reduced, so that at least 80%, more preferably at least 90%, and most preferably at least 95%, or more, of the complex N-glycan antennae of the recombinant glycoprotein are not fucosylated.

In this aspect, all relevant definitions and limitations given above for the first and second aspect of the present invention apply in an analogous manner.

Respective recombinant glycoproteins can be produced as described herein, e.g. by overexpression of ST6Gal1 and/or ST3Gal4 together with the recombinant glycoprotein. Preferably, said glycoproteins are produced in a cell line according to the present invention as described herein.

In a fourth aspect, the present invention relates to a method for the expression of a recombinant glycoprotein according to the present invention, comprising the steps of:
(a) providing a cell line according to the present invention,
(b) expressing the recombinant glycoprotein in said cell line; and
(c) isolating the recombinant glycoprotein from the cells or the cell culture supernatant.

In this aspect, all relevant definitions and limitations given above for the first, second and third aspect of the present invention apply in an analogous manner. In particular, the recombinant glycoprotein and the cell line are as defined above.

Means for the expression of proteins in the cell lines of the present invention are not particularly limited and are known in the art. In this context, the step (b) of expressing the glycoprotein of interest in said cell line encompasses the transfection of a respective coding nucleic acid into said cell line prior to the actual expression of the glycoprotein. Further, means for isolating a glycoprotein of interest from a cell culture are not particularly limited and are known in the art.

In a related aspect, the present invention relates to the use of a cell line according to the present invention for the production of recombinant glycoproteins according to the present invention.

In this aspect, all of the definitions and preferred and/or specific embodiments described for the recombinant glycoproteins of the present invention and the cell lines of the present application apply in an analogous manner where applicable.

The figures show:

FIG. 1:
The Lewis glyco-epitope family, showing a subset of possible variants. The $Le^X$ glyco-epitopes carry fucose in an α1-3 linkage to the GlcNAc monosaccharide. A) sialylated, non-fucosylated GlcNAc; B) Lewis X ($Le^X$) also called CD15 or SSEA-1; C) Sialyl Lewis X ($sLe^X$).

Figure 2:
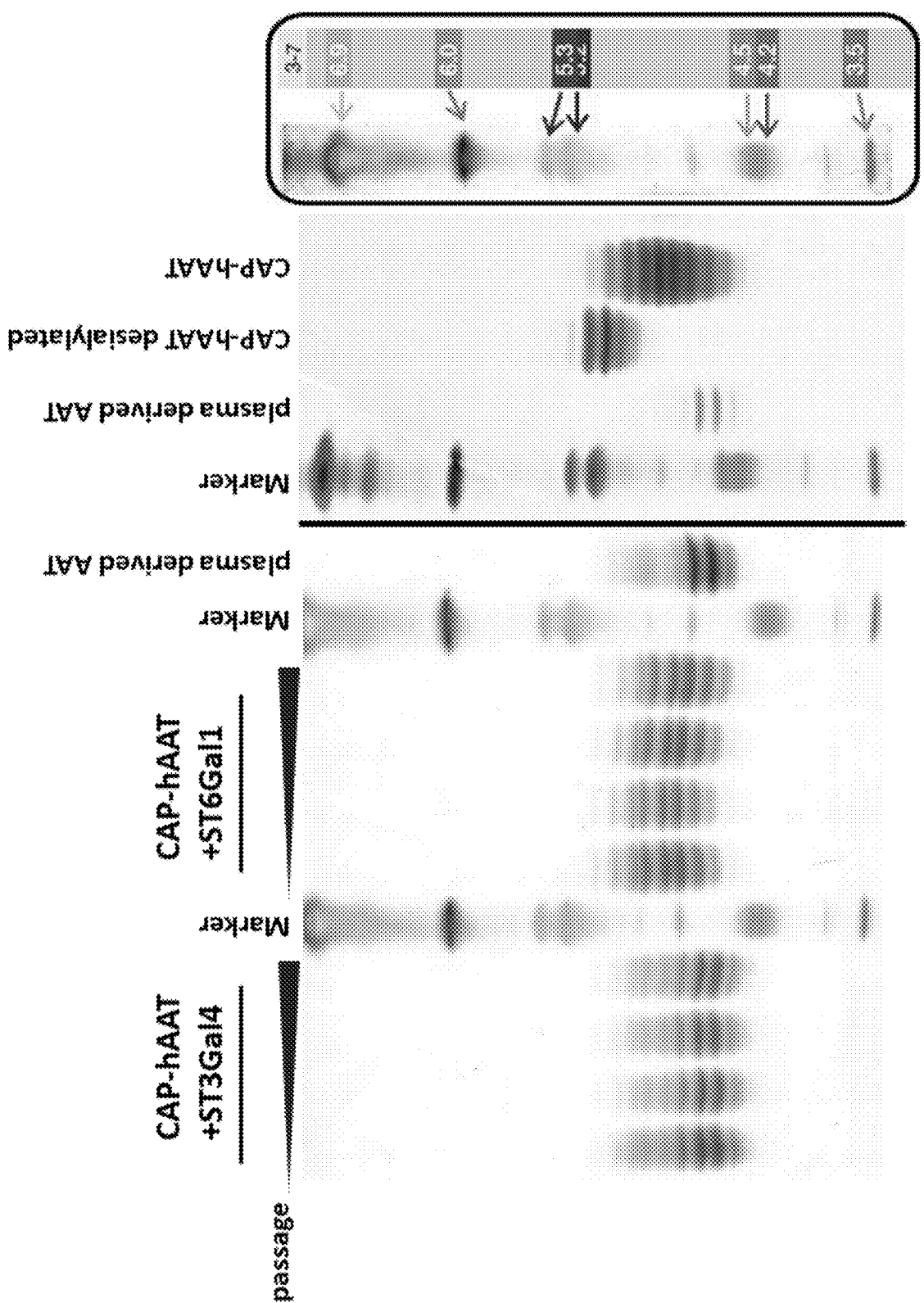

FIG. 2:
IEF (isoelectric focusing) analysis shows increased sialylation of hAAT purified from glyco-optimized CAP cells stably, recombinantly expressing hAAT and ST3Gal4 or ST6Gal1 compared to hAAT purified from non-engineered hAAT expressing CAP cells. 5 µg of affinity purified hAAT per lane were subjected to isoelectric focusing. Different time points during pool generation are shown. Samples: CAP-hAAT-ST3Gal4, hAAT from CAP cell stably expressing human AAT as well as sialyltransferase ST3Gal4, CAP-hAAT-ST6Gal1, hAAT from CAP cell stably expressing human AAT as well as sialyltransferase ST6Gal1. Plasma derived hAAT (Prolastin), hAAT from non-glyco-optimized CAP cells, and desialylated hAAT from CAP cells served as controls.

Figure 3:
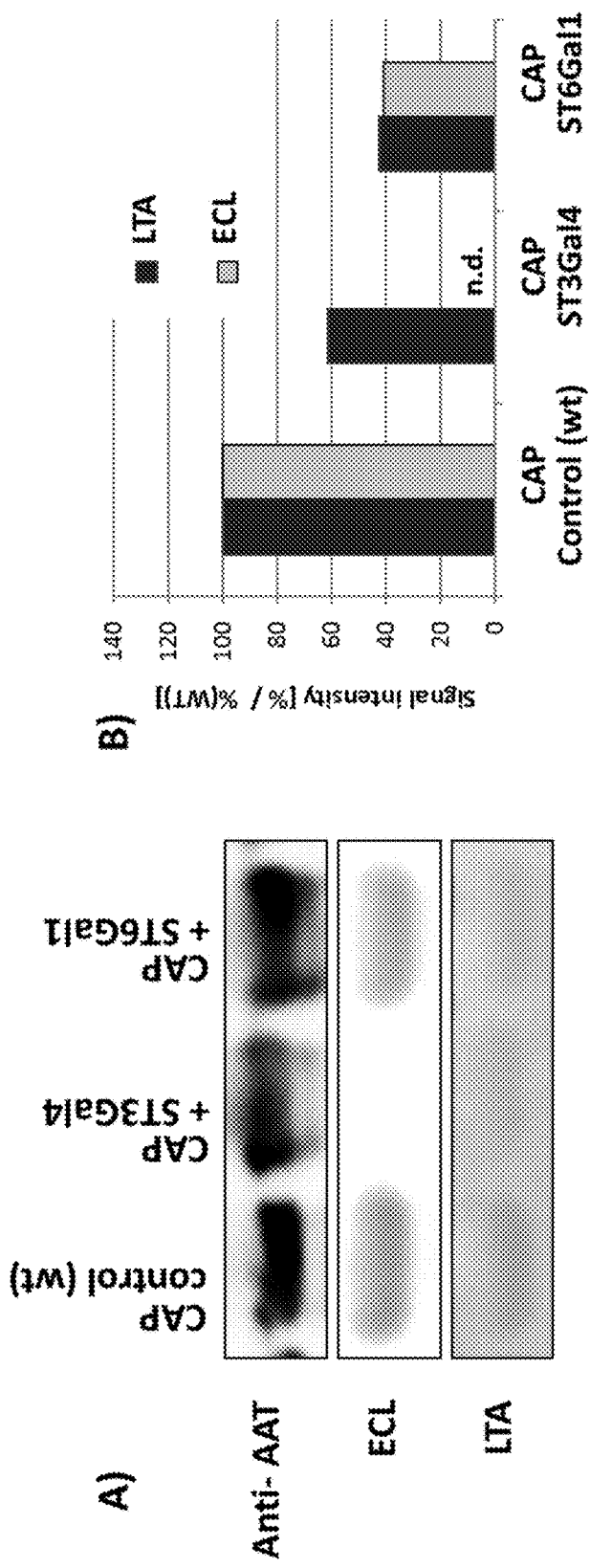

FIG. 3:
Comparative lectin blot analysis of recombinant AAT reveals that a decreased amount of fucosylation correlates with increased amounts of sialylation. Purified human rAAT from either wild-type CAP cells, CAP-ST3Gal4 cells or CAP-ST6Gal1 cells were separated by SDS-PAGE, blotted on nitrocellulose membrane and detected by specific lectins. The corresponding densitometrical analysis (B) was normalized on the AAT protein content in the matching western blot. The *Erythrina crista-galli* lectin (ECL-lectin) analysis detects free galactoses on N-glycans which indicates incomplete sialylation. α1-3 linked fucose is detected by *Lotus tetragonolobus* agglutinin (LTA).

Figure 4:
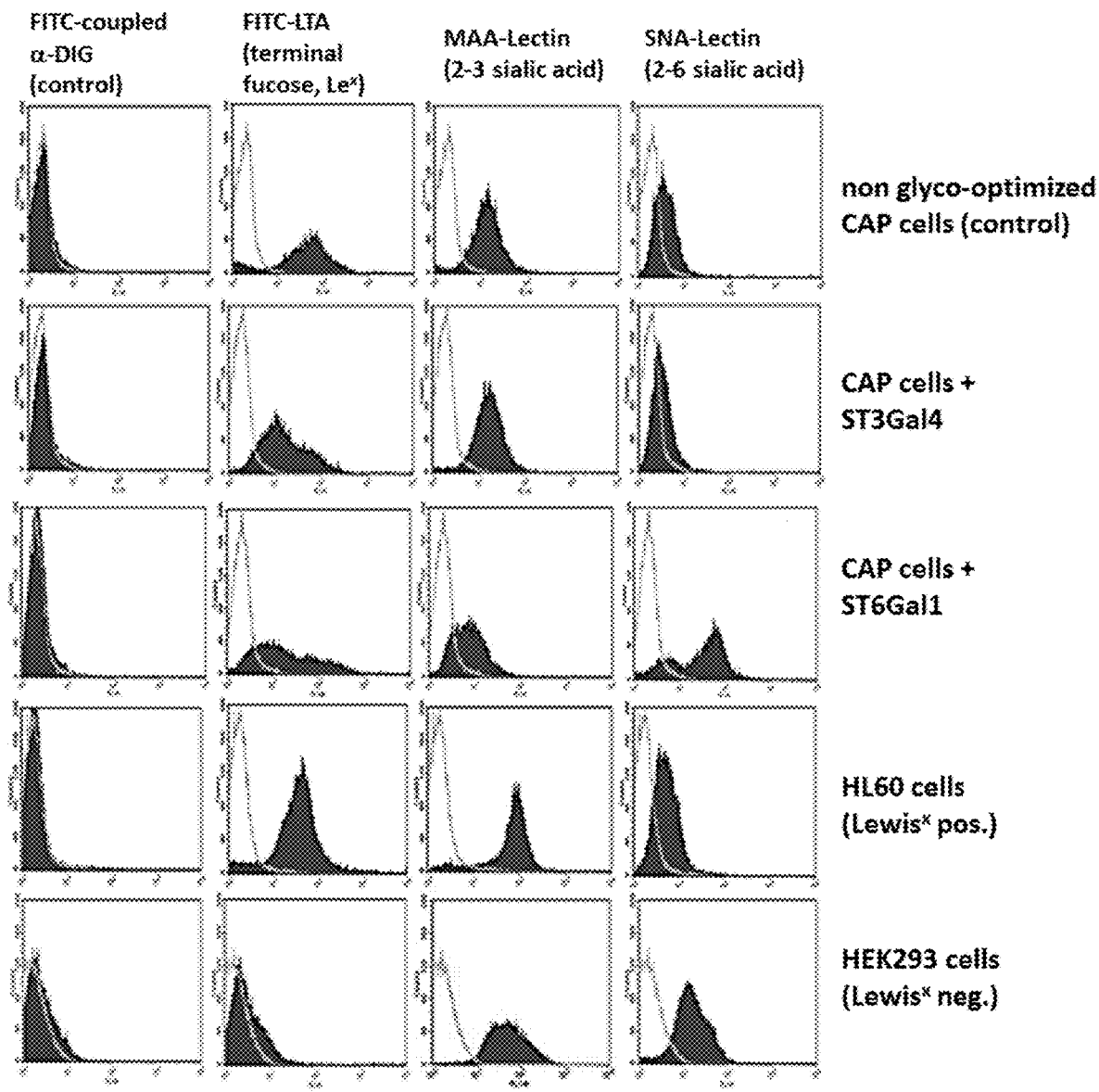

FIG. 4:
FACS analysis of cell surface glycoproteins of glyco-optimized CAP cells stably expressing ST3Gal4 or ST6Gal1 in comparison to non-engineered CAP cells reveals that overexpression of one of these two sialyltransferases not only increases the degree of sialylation on the majority of expressed glycoproteins. It also decreases the amount of antennary fucose on N-glycan structures, resulting in a reduced amount of $Lewis^X$ structures.

Figure 5:
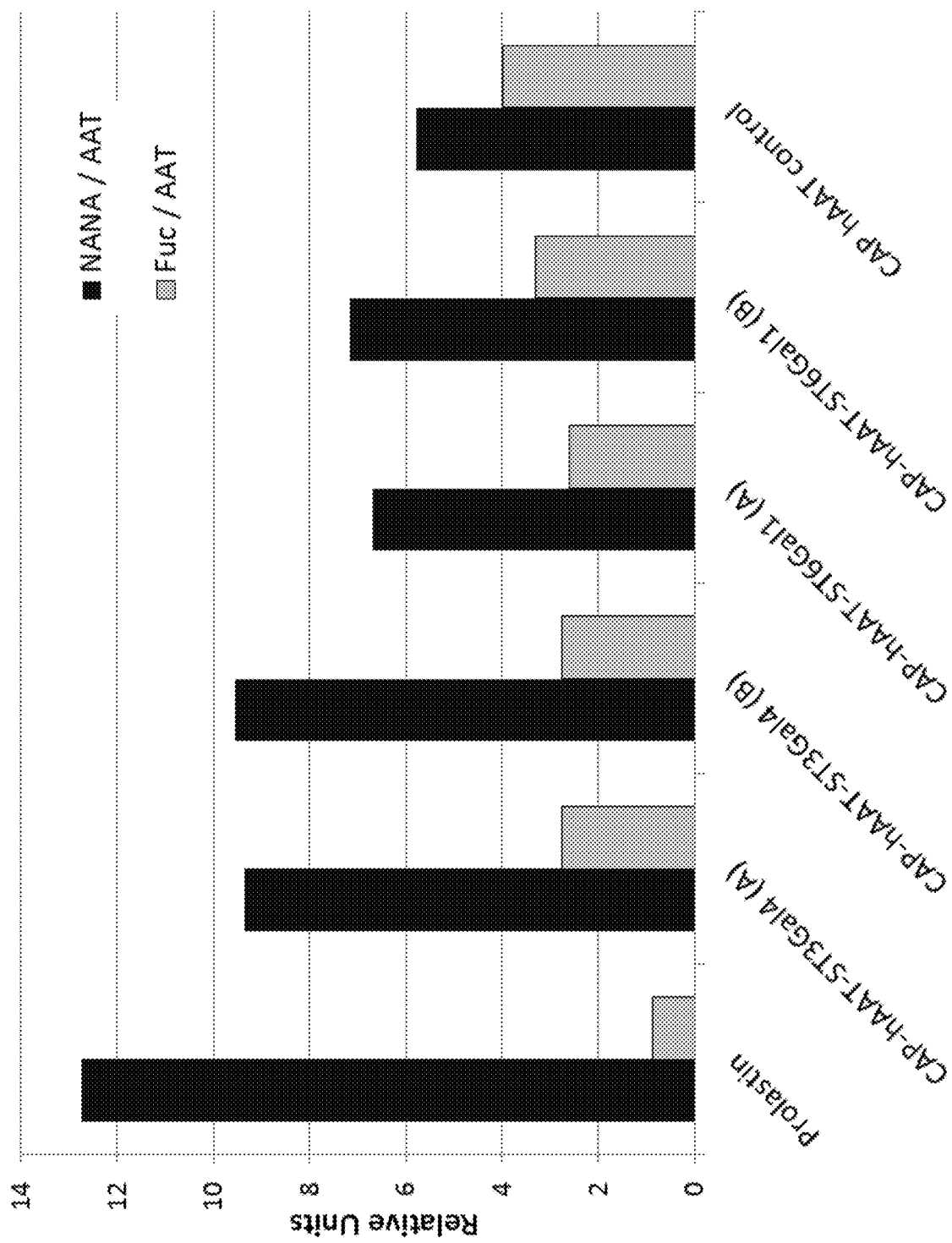

FIG. 5:
Increasing amounts of sialic acid (NANA) and reduced amounts of fucose (Fuc) in hAAT purified from CAP cells stably expressing either ST3Gal4 or ST6Gal1 compared to hAAT purified from cell culture supernatant from non-engineered CAP cells. Plasma derived hAAT (Prolastin) shown as control. Monosaccharide analysis was performed by high performance anion exchange chromatography with pulsed amperometric detection (HPAEC PAD).

Figure 6:
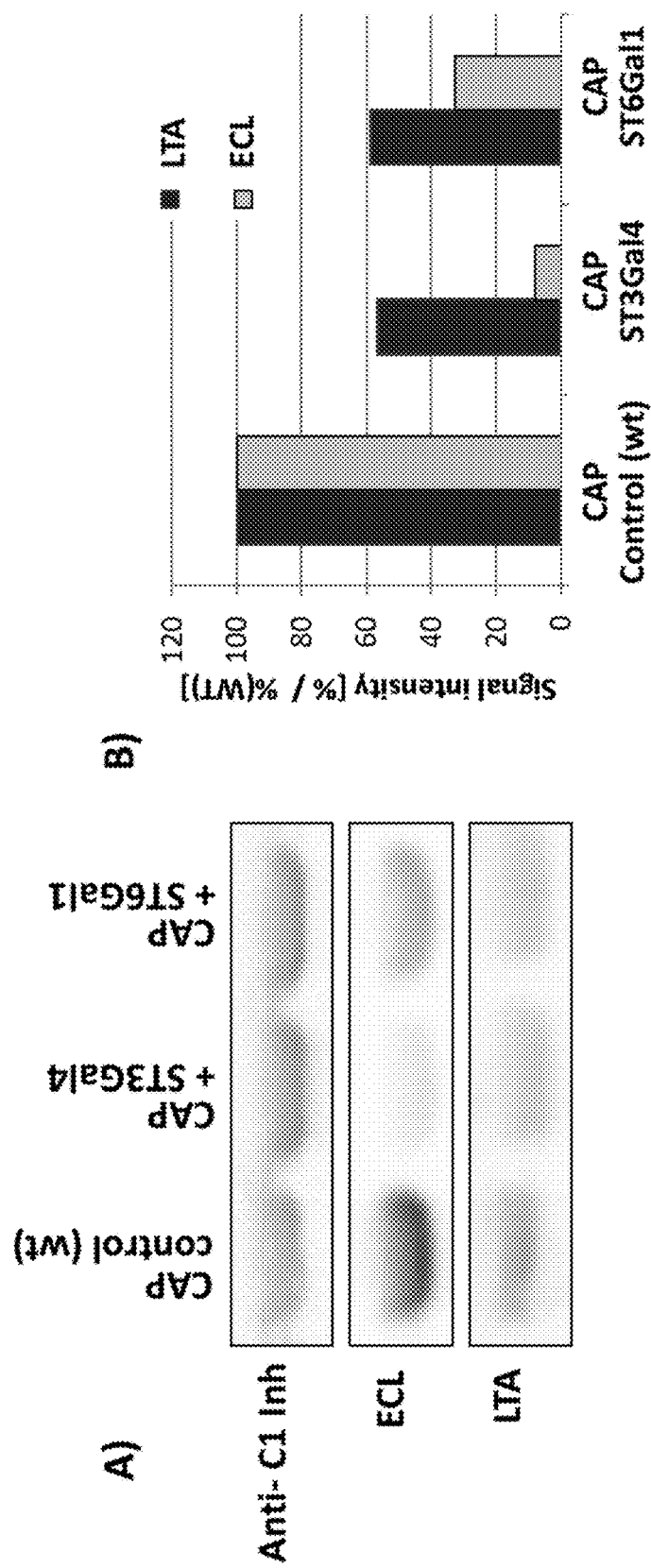
Figure 7A:
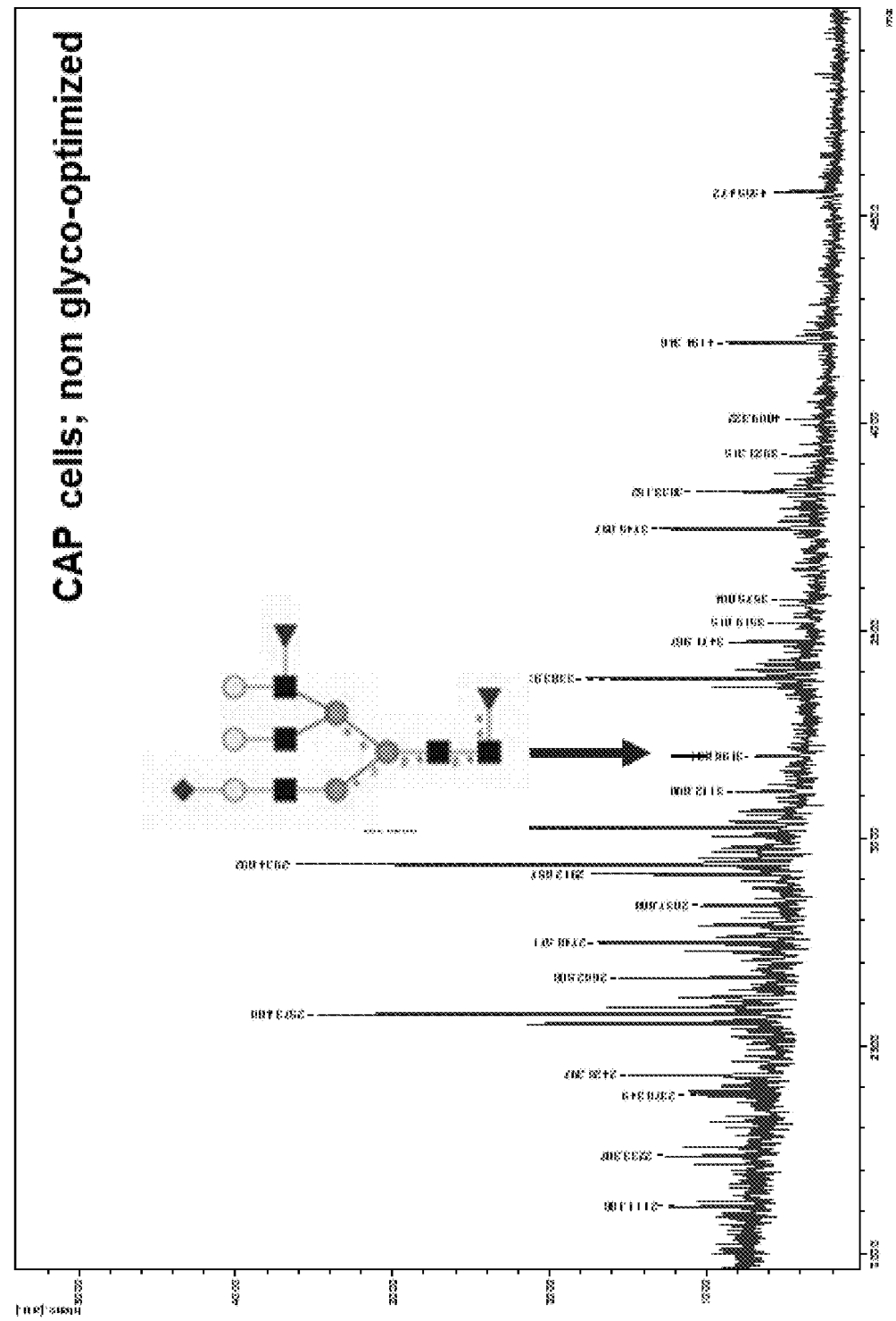
Figure 7B:
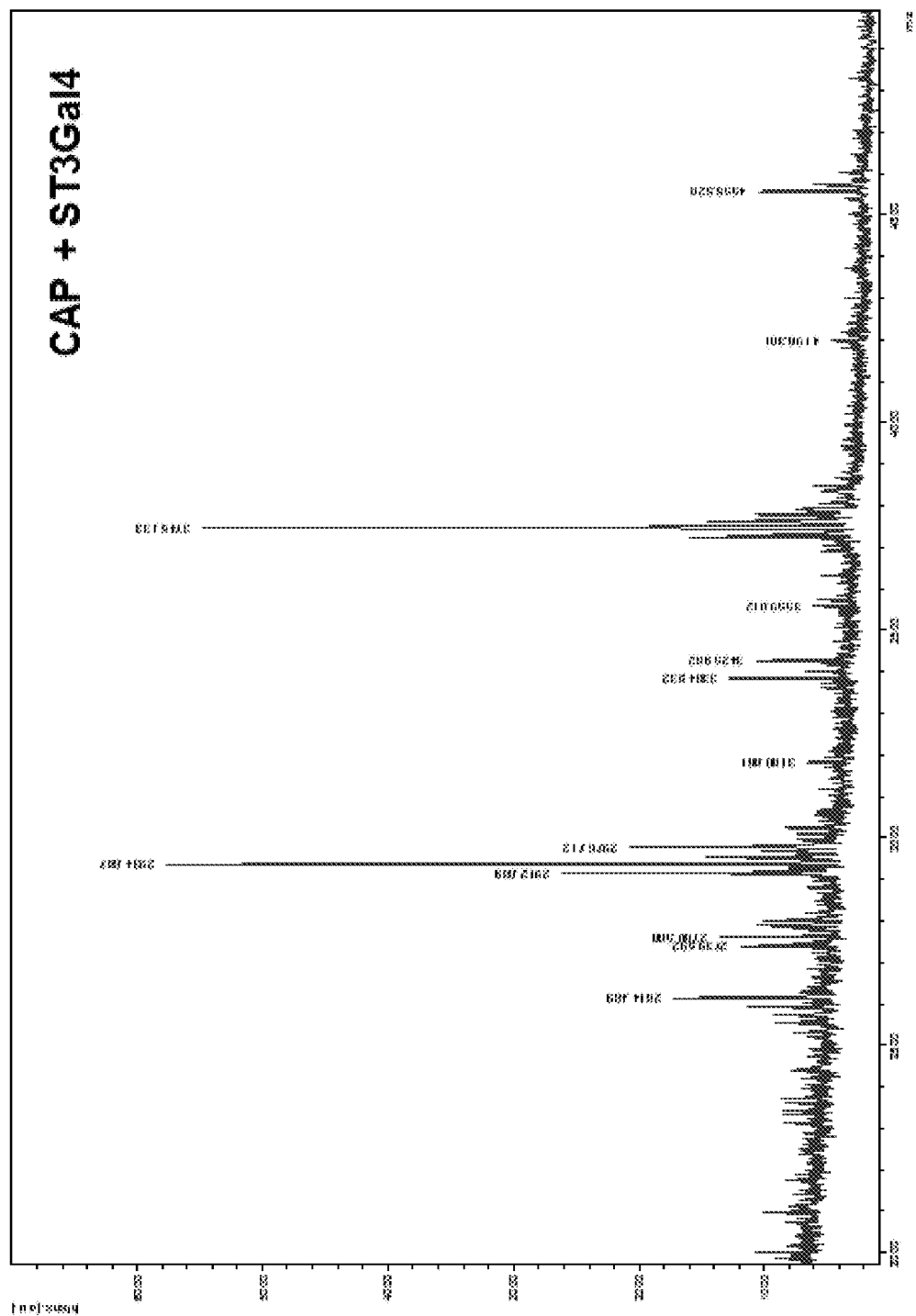
Figure 7C:
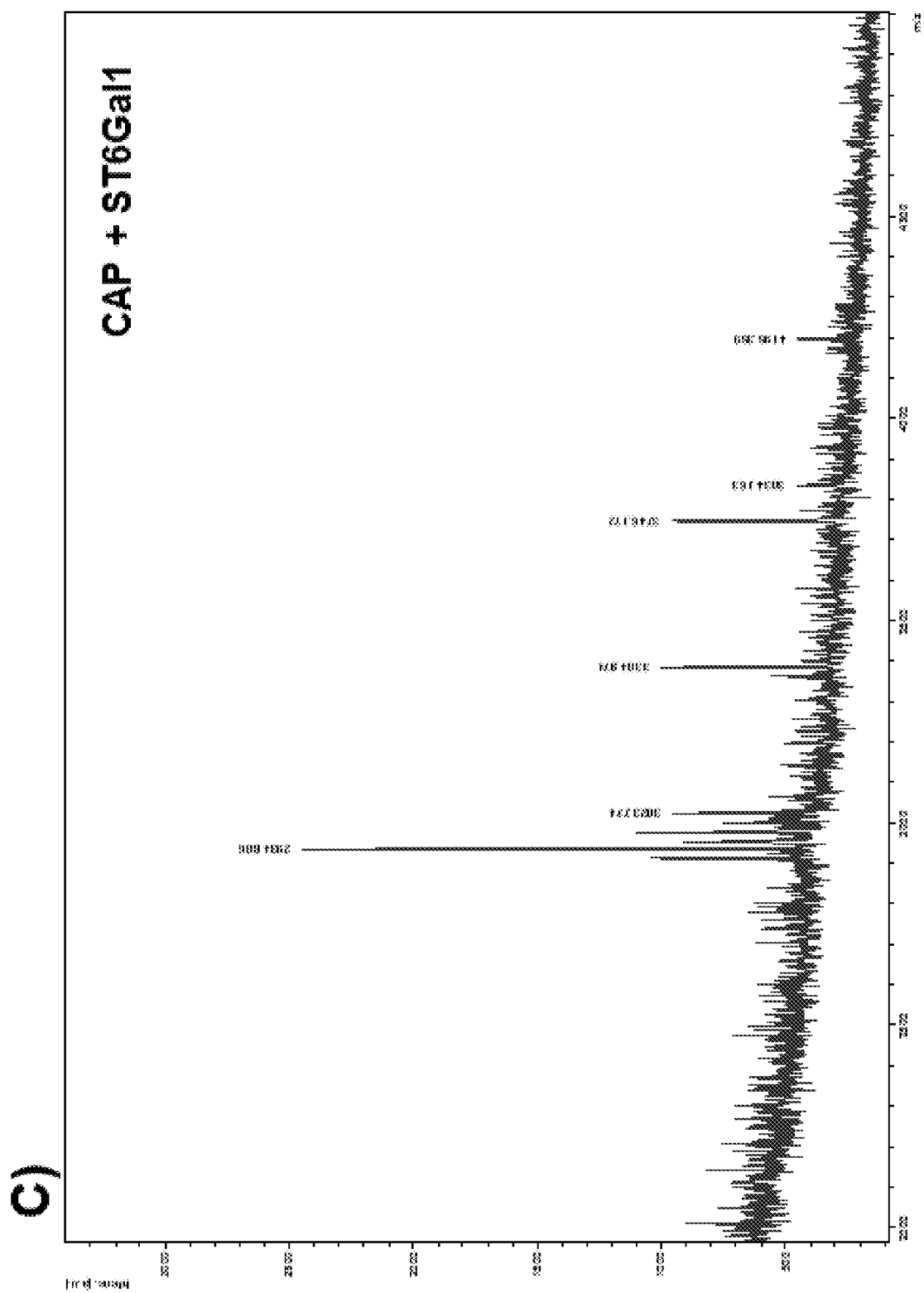
Figure 7D:
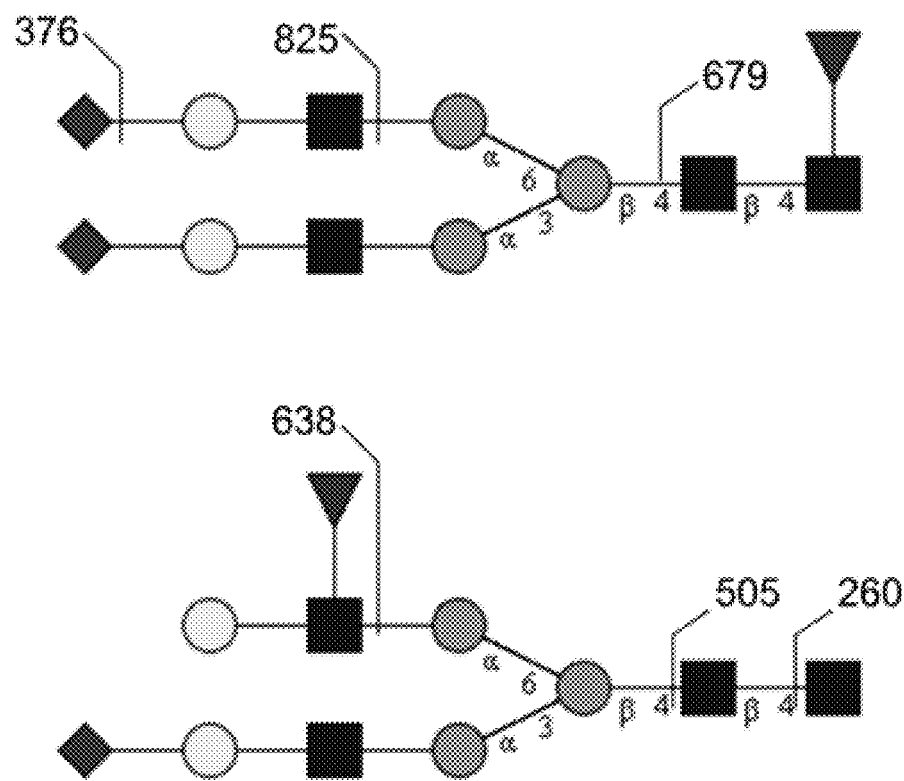

FIG. 6:
Comparative lectin blot analysis of recombinant C1-Inhibitor reveals that an increase in sialylation correlates with a decrease in antennary fucosylation. Purified C1-Inhibitor from either wild-type CAP cells, CAP-ST3Gal4 cells or CAP-ST6Gal1 cells were separated by SDS-PAGE, blotted on nitrocellulose membrane and detected by specific lectins. The corresponding densitometrical analysis (B) was normalized to the C1-Inh protein content in the matching western blot. The *Erythrina crista-galli* lectin (ECL-lectin) analysis (A and B) detects free galactoses on N-glycans which indicates incomplete sialylation. α1-3 linked fucose is detected by *Lotus tetragonolobus* agglutinin (LTA).

FIG. 7:

MS-MS analysis of recombinant C1-Inhibitor: PNGase F released permethylated N-glycans from purified C1-Inhibitor either from wild-type CAP cells, from CAP-ST3Gal4 cells or from CAP-ST6Gal1 cells were analyzed by MALDI TOF/TOF. Only the signal at 3196.8 in MS1 of wildtype derived C1-Inhibitor (A) contained two fucose residues and the characteristic fragmentation pattern for antennary fucose (M/z 638, 505, 260; D) in MS2. In CAP-ST3Gal4 (B) and CAP-ST6Gal1 (C) the signal at 3196.8 could not be detected, also no other signal of MS1 contained a fragmentation pattern of antennary fucose in MS2.

The present invention will be further illustrated in the following examples without being limited thereto.

EXAMPLES

Experimental Procedures:
Cell Culture and Fermentation.

The permanent human amniocyte cell line CAP 1D5 was cultured in suspension, either in chemically defined, animal component free CAP-CDM medium (CEVEC Pharmaceuticals, Germany) supplemented with 6 mM stable glutamine (Biochrom, Germany), or in serum free PEM media (Life Technologies) supplemented with 4 mM stable glutamine (Biochrom, Germany). CAP cells were cultivated at 37° C. in shaker flasks (Corning, #431143, 125 mL (25 mL wv) or #431252, 3000 mL (1000 mL wv)) at 5% $CO_2$, and 185 rpm. During fermentation, CAP cells were fed at d3, d5, and d7 with 10% CAP-CDM feed solution (CEVEC Pharmaceuticals, Germany) and 4 mM stable glutamine (Biochrom, Germany).

Cloning.

For the generation of CAP cell lines stably expressing ST3Gal4 or ST6Gal1, the cells were nucleofected with the corresponding nucleic acid constructs. Table 1 lists all cell lines created for this project.

For designing the ST3Gal4 cDNA, sequence information of the precursor protein and mature protein was based on the database entry UniProt Q11206 (SEQ ID NO: 1). For cloning, a ClaI restriction site and a Kozak sequence were added 5' of the start codon of the human ST3Gal4 cDNA and an EcoRV restriction site was added 3' of the stop codon to be inserted between the ClaI and EcoRV restriction sites in the pStbl-Neo-CMV-MCS(−) vector resulting in the expression plasmid pStbl-Neo-CMV-ST3Gal4. This vector contains a CMV promoter driving the expression of the gene of interest, followed by an SV40 intron for improved, splicing-mediated mRNA transport and a multiple cloning site for the insertion of the gene of interest. The selection marker is driven by the human ubiquitin (UbC) promoter. cDNA synthesis was performed at GeneArt (Germany, Life Technologies).

For designing the ST6Gal1 cDNA, sequence information of the precursor protein and mature protein was based on the database entry UniProt P15907 (SEQ ID NO: 2). For cloning, a ClaI restriction site and a Kozak sequence were added 5' of the start codon of the human ST6Gal1 cDNA and an EcoRV restriction site was added 3' of the stop codon to be inserted between the ClaI and EcoRV restriction sites in the pStbl-Neo-CMV-MCS(−) vector resulting in the expression plasmid pStbl-Neo-CMV-ST6Gal1. cDNA synthesis was performed at GeneArt (Germany, Life Technologies).

Nucleofection and Pool Generation.

Nucleofection was performed using a Nucleofector II (LONZA) with the appropriate Nucleofector Kit (KitV) according to the manufacturer's protocol. Briefly, during exponential growth phase of the culture $1 \times 10^7$ cells were harvested via centrifugation (150 g for 5 min) and re-suspended in 100 µl complete Nucleofector solution and mixed with a total of 5 µg plasmid. Nucleofection was performed using the X001 program. After the pulse, cells were recovered in 12 ml complete cell culture media in a 125 ml shaking flask. The cells were cultured as before at 37° C., 5% $CO_2$, and 185 rpm.

72 to 96 h post-nucleofection cells were selected with 200 µg/ml neomycin in order to generate stable pools.

Western Blot Analysis.

Purified protein solutions were separated on a NuPAGE Novex 4-12% Bis-Tris Gel under reducing conditions, according to the manufacturer's instructions. The separated proteins were transferred via a Blot Module (Invitrogen) (30 V for 60 min at RT) onto an Amersham Hybond ECL membrane (100 V for 60 min at RT). The membrane was blocked for 1 h at RT with PBSTB (phosphate-buffered saline, pH=7.4, supplemented with 0.1% Tween 20 and 1% BSA). Afterwards, the membrane was incubated with the specific horseradish peroxidase (HRP)-labeled antibody diluted in PBSTB. After washing the membrane with PBST (phosphate-buffered saline pH=7.4 supplemented with 0.1% Tween 20), the proteins were detected using the Pierce ECL WB Substrate Kit via a chemiluminescence detector (INTAS).

Lectin Immunoblotting.

Lectins are proteins that bind specific carbohydrate structures. Biotin-coupled lectins can therefore be used to analyze N-linked glycans. *Erythrina crista-galli* (ECL) lectin detects β1-4 linked terminal galactose on N-linked glycans, *Sambucus nigra* agglutinin (SNA) preferentially binds to α2,6-linked sialic acid, whereas *Maackia amurensis* lectin (MAL) preferentially binds to α2,3-linked sialic acids. α1-3 linked fucose is detected by *Lotus tetragonolobus* agglutinin (LTA) and *Aleuria aurantia* lectin (AAL) detects α1-2-, -3, or -6 linked fucose.

Purified protein solutions from parental CAP cells with or without co-expression of ST3Gal4 and/or ST6Gal1 were separated as described above and blotted onto Amersham Hybond ECL nitrocellulose membrane (GE healthcare). The membrane was blocked for 1 h at RT with PBSTB (phosphate-buffered saline, pH=7.4, supplemented with 0.1% Tween 20 and 1% BSA). Afterwards, the membrane was incubated with the lectin diluted in PBSTB. After washing the membrane with PBST (phosphate-buffered saline, pH=7.4, supplemented with 0.1% Tween 20), the membrane was stained with streptavidin-coupled horseradish peroxidase (HRP) for 1 h at RT (diluted in PBSTB). The HRP signal was amplified using anti-streptavidin IgG and anti IgG-HRP. The proteins were detected using the Pierce ECL WB Substrate Kit via a chemiluminescence detector (INTAS).

TABLE 1

Stable cell lines used in the present invention.

| Cell line | rec. protein | overexpression of the sialyltransferase(s) |
| --- | --- | --- |
| CAP | / | / |
| CAP-AAT | AAT | / |
| CAP-AAT-ST3Gal4 | AAT | ST3Gal4 |
| CAP-AAT-ST6Gal1 | AAT | ST6Gal1 |
| CAP-C1 Inh | C1 Inh | / |
| CAP-C1 Inh-ST3Gal1 | C1 Inh | ST3Gal4 |
| CAP-C1 Inh-ST3Gal4 | C1 Inh | ST6Gal1 |

Isoelectric Focusing (IEF) Analysis.

Isoelectric focusing (IEF) was performed in order to analyze the isoelectric point (pI) of rhAAT purified from CAP cells expressing rhAAT with or without additional expression of ST3Gal4 or ST6Gal1. The degree of sialylation correlates with a given proteins acidity and, therefore, with its pI. IEF analysis was done according to the manufacturers protocol (Invitrogen). Briefly, 5 µg of purified protein were loaded on pH 3-7 gels and subjected to electrophoresis (1 h 100 V, 1 h 200 V, 30 min 500 V). Proteins were stained with SimplyBlue SafeStain according to the manufacturer's protocol (Invitrogen).

Example 1

Significantly Reduced Amount of Lewis$^X$ Structures on hAAT Protein Purified from CAP-ST3Gal4 or ST6Gal1 Cells.

α1-Antitrypsin (AAT) is a protease inhibitor belonging to the serpin superfamily. AAT is a potent inhibitor of serine proteases, in particular neutrophil elastase. AAT is a 52 kDa glycoprotein carrying 3 N-glycosylation sites.

Cells of the human amniocyte cell line CAP already stably expressing human AAT were additionally stably transfected with a plasmid encoding either the sialyltransferase ST3Gal4 to achieve an increase in 2,3-linked sialylation of terminal galactose of N-glycans or the sialyltransferase ST6Gal1 to achieve an increase in 2,6-sialylation of terminal galactose of N-glycans.

Enhanced 2,3- or 2,6-sialylation upon overexpression of sialyltransferase ST3Gal4 or ST6Gal1 were determined by isoelectric focusing (IEF) analysis of purified hAAT (FIG. 2).

As the backbones of the different rhAAT (recombinant hAAT) are identical, changes in the IEF indicate changes in the sialic acid content. Recombinant hAAT expressed in CAP cells with additional expression of ST3Gal4 results in a modified rhAAT which shifts significantly towards an acidic pI indicating an increased extent of sialylation; rhAAT expressed in parental CAP cells overexpressing ST6Gal1 also shifts towards a more acidic pI but to a lower degree (FIG. 2). This is probably due to the different substrate affinities of ST3Gal4 and ST6Gal1. ST6Gal1 catalyzes sialylation of the primary branches of N-glycans, whereas ST3Gal4 catalyzes the sialylation of the primary branches of N-glycan as well as the additional branches of tri- and tetra-antennary N-glycans. Therefore, ST3Gal4 has more acceptor substrate available than ST6Gal1.

This result could be confirmed via lectin blot analysis (FIG. 3). Increased amounts of α2,3- or α2,6-sialylation upon overexpression of sialyltransferase ST3Gal4 or ST6Gal1 were determined via *Erythrina crista-galli* (ECL) lectin blot analysis. ECL lectin detects β1-4 linked terminal galactose on N-linked glycans. Therefore, a diminished signal in the ECL blot correlates to an increased amount of sialylation. Purified AAT from control CAP cells expressing AAT shows a clear signal in the ECL lectin blot, proving an incomplete sialylation. AAT derived from ST6Gal1 or ST3Gal4 overexpressing CAP cells, showed a strong reduction or complete absence of the ECL signal, indicating that only minimal amounts of unsialylated β1-4 linked galactose on the N-linked glycan exist in these preparations (FIG. 3).

Remarkably, the degree of antennary fucose (Lewis$^x$ antigen) is reduced on rhAAT upon co-expression of ST6Gal1 or ST3Gal4 as proven by the reduced signal intensity in the *Lotus tetragonolobus* agglutinin (LTA Lectin) blot analysis in FIG. 3. *Lotus tetragonolobus* agglutinin (LTA) specifically detects the α1-3 linked antennary fucose. Therefore, overexpression of the sialyltransferases ST3Gal4 and ST6Gal1 is an unexpected but appropriate way to significantly reduce the amount of the unwanted and potentially immunogenic Lewis$^x$ structures on N-linked glycans.

Example 2

FACS Analysis of Glycoproteins on the Cell Surface of CAP Cells Expressing ST3Gal4 or ST6Gal1.

In order to determine the degree of fucosylation of glycoproteins on the cell surface with increased degree of sialylation by overexpression of sialyltransferases, flow cytometry (FACS) analyses was performed (FIG. 4).

CAP-hAAT-ST3Gal4 or CAP-hAAT-ST6Gal1 cells were stained with different antibodies and lectins to analyze sugar epitopes on the surface of the cells. Typically, 1×10$^7$ cells were centrifuged for 10 min at 140×g and re-suspended into 100 µl PBS/BSA. 10 µl (10$^6$ cells) were mixed with 10 µl of antibody or lectin (1 mg/ml; FITC conjugated or DIG coupled in combination with a FITC coupled anti-DIG antibody) and 90 µl PBS/BSA were added. After 10 min at 4° C., the cells were washed with PBS/BSA. Cell pellets were re-suspended into 500 µl PBS/BSA and subjected to FACS analysis on a Becton Dickinson FACSCalibur flow cytometer. Dead cells were identified and excluded by staining with propidium iodide. Typically, 30000 events were counted and analyzed. FITC or PE stained cells were graphically overlaid with unstained cells.

FIG. 4 shows parental CAP-hAAT cells or CAP-hAAT cells stably expressing α2,3 (CAP-hAAT+ST3Gal4) or α2,6 (CAP-hAAT+ST6Gal1) sialyltransferase, respectively. Cells were either stained with lectins specific for α2,3 coupled neuraminic acid, MAA (*Maackia amurensis* agglutinin), or α2,6 coupled neuraminic acid residues, SNA (*Sambucus nigra* agglutinin), or with LTA (*Lotus tetragonolobus* agglutinin) recognizing α1,3 linked fucose residues (Le$^X$). Parental CAP-hAAT, HL60 (Le$^X$ pos.), Le$^X$ negative HEK293 cells (Le$^X$ neg.) as well as cells incubated with the FITC coupled anti-DIG antibody only are shown as controls.

As expected, overexpression of α2,3- or α2,6-sialyltransferase increases the respective coupled neuraminic acid residues on the N-glycans of cell surface glycoproteins. Interestingly, expression of ST3Gal4 or ST6Gal1 reduces the amount of the non-preferred Le$^x$ structures on glycoproteins on the cell surface, as indicated by significantly reduced staining with lectin LTA.

Example 3

Monosaccharide Analysis of hAAT Expressed in CAP-ST3Gal4 or CAP-ST6Gal1 Cells by HPAEC PAD Analysis.

In order to determine if the total amount of sialic acid and fucose of purified recombinant hAAT from CAP cells changes upon additional expression of the sialyltransferases ST3Gal4 or ST6Gal1, a monosaccharide analysis by high performance anion exchange chromatography with pulsed amperometric detection (HPAEC PAD) was performed.

FIG. 5 shows the relative amounts of sialic acid and fucose as determined by monosaccharide analysis via HPAEC-PAD in CAP-hAAT cells either stably transfected with a plasmid encoding ST3Gal4 or ST6Gal1.

FIG. 5 reveals that by expressing human sialyltransferases, sialic acid content is elevated, whereas the amount of fucose per rhAAT molecule is significantly reduced relative to an un-transfected control, indicating that the amount of the non-preferred Le$^x$ or sialyl-Le$^x$ structure is reduced upon overexpression of sialyltransferases. Of note in this experiment, the total amount of fucose was determined without differentiating between antennary fucose residues (α1-3 linked fucose) and core fucose (α1-6 linked fucose) of N-glycans. As additional expression of sialyltransferases only affects the amount of antennary α1-3 linked fucose but not the relatively abundant core fucose, the determined overall reduction of fucose upon overexpression of sialyltransferases of 25% (ST6Gal1) and 30% (ST3Gal4) indicates a pronounced reduction in the absolute amount of antennary α1-3 linked fucose.

The overall reduction in fucose residues is very surprising as the distal GlcNAc from sialylated complex N-glycans (NeuAc(α1->4)Gal(ß1-4)GlcNAc-R), which will be increased upon overexpression of ST3Gal4 and/or ST6Gal1, is a substrate for the fucosyltransferases Fut5, Fut6, and Fut7. Therefore, overexpression of sialyltransferases as ST3Gal4 should rather result in an increase in sialyl-Lewis$^x$ structures than an overall decrease in fucose residues.

Example 4

Reduced Amount of Lewis$^x$ Structures on hC1 Inhibitor Protein Purified from CAP-ST3Gal4 or ST6Gal1 Cells.

Cells of the human amniocyte cell line CAP-hC1 Inh were stably transfected with a plasmid encoding either the sialyltransferase ST3Gal4 to achieve increased α2,3-linked sialylation of terminal galactose of N-glycans or sialyltransferase ST6Gal1 to achieve increased α2,6-sialylation of terminal galactose of N-glycans.

Increased amounts of α2,3- or α2,6-sialylation upon overexpression of sialyltransferase ST3Gal4 or ST6Gal1 were determined via *Erythrina crista-galli* (ECL) lectin blot analysis. ECL lectin detects β1-4 linked terminal galactose on N-linked glycans. As shown in FIG. 6, overexpression of ST3Gal4 results in an increased sialylation of the N-linked glycans in comparison to C1 Inh purified from cell culture supernatant from non-glycomodified CAP cells. Overexpression of ST6Gal1 also results in an increased sialylation of terminal galactose on N-linked glycans in comparison to the non-glycomodified C1-Inh, although the effect is not as pronounced as upon overexpression of ST3Gal4. This is most likely due to the different substrate affinities of ST3Gal4 and ST6Gal1 as explained in Example 1.

The amount of antennary α1-3 linked fucose in the different C1 Inh protein preparations (CAP control, CAP-ST3Gal4, CAP-ST6Gal1) was determined by the *Lotus tetragonolobus* agglutinin (LTA) blot analysis. FIG. 6 reveals that the increased sialylation upon overexpression of ST6Gal1 or ST3Gal4 correlates with a reduced amount of antennary fucosylation proven by the decreased signal intensity in the LTA lectin blot analysis.

These results were confirmed by MS-MS analysis of N-glycans from C1 Inh derived in CAP control cells, CAP-ST3Gal4, or CAP-ST6Gal1 cells (FIG. 7). PNGaseF released permethylated N-glycans from purified C1-Inhibitor either from control CAP cells, from CAP-ST3Gal4 cells or from CAP-ST6Gal1 cells were analyzed by MALDI TOF/TOF. Only the signal at 3196.8 in MS1 in wildtype derived C1-Inhibitor (FIG. 7 A) contained two fucose residues and the characteristic fragmentation pattern for antennary fucose (M/z 638, 505, 260; D) in MS2. In CAP-ST3Gal4 and CAP-ST6Gal1 (FIGS. 7 B and C) the signal at 3196.8 could not be detected. Moreover, no other signal of MS1 contained a fragmentation pattern of antennary fucose in MS2.

The present invention relates to the following amino acid sequences.

Human ST3Gal4
SEQ ID NO: 1
MVSKSRWKLLAMLALVLVVMVWYSISREDRYIELFYFPIPEKKEPCLQGE
AESKASKLFGNYSRDQPIFLRLEDYFWVKTPSAYELPYGTKGSEDLLLRV
LAITSSSIPKNIQSLRCRRCVVVGNGHRLRNSSLGDAINKYDVVIRLNNA
PVAGYEGDVGSKTTMRLFYPESAHFDPKVENNPDTLLVLVAFKAMDFHWI
ETILSDKKRVRKGFWKQPPLIWDVNPKQIRILNPFFMEIAADKLLSLPMQ
QPRKIKQKPTTGLLAITLALHLCDLVHIAGFGYPDAYNKKQTIHYYEQIT
LKSMAGSGHNVSQEALAIKRMLEMGAIKNLTSF Human ST6Gal1
SEQ ID NO: 2
MIHTNLKKKFSCCVLVFLLFAVICVWKEKKKGSYYDSFKLQTKEFQVLKS
LGKLAMGSDSQSVSSSSTQDPHRGRQTLGSLRGLAKAKPEASFQVWNKDS
SSKNLIPRLQKIWKNYLSMNKYKVSYKGPGPGIKFSAEALRCHLRDHVNV
SMVEVTDFPFNTSEWEGYLPKESIRTKAGPWGRCAVVSSAGSLKSSQLGR
EIDDHDAVLRFNGAPTANFQQDVGTKTTIRLMNSQLVTTEKRFLKDSLYN
EGILIVWDPSVYHSDIPKWYQNPDYNFFNNYKTYRKLHPNQPFYILKPQM
PWELWDILQEISPEEIQPNPPSSGMLGIIIMMTLCDQVDIYEFLPSKRKT
DVCYYYQKFFDSACTMGAYHPLLYEKNLVKHLNQGTDEDIYLLGKATLPG
FRTIHC Human AAT
SEQ ID NO: 3
MPSSVSWGILLLAGLCCLVPVSLAEDPQGDAAQKTDTSHHDQDHPTFNKI
TPNLAEFAFSLYRQLAHQSNSTNIFFSPVSIATAFAMLSLGTKADTHDEI
LEGLNFNLTEIPEAQIHEGFQELLRTLNQPDSQLQLTTGNGLFLSEGLKL
VDKFLEDVKKLYHSEAFTVNFGDTEEAKKQINDYVEKGTQGKIVDLVKEL
DRDTVFALVNYIFFKGKWERPFEVKDTEEEDFHVDQVTTVKVPMMKRLGM
FNIQHCKKLSSWVLLMKYLGNATAIFFLPDEGKLQHLENELTHDIITKFL
ENEDRRSASLHLPKLSITGTYDLKSVLGQLGITKVFSNGADLSGVTEEAP
LKLSKAVHKAVLTIDEKGTEAAGAMFLEAIPMSIPPEVKFNKPFVFLMIE
QNTKSPLFMGKVVNPTQK Human C1 Inh
SEQ ID NO: 4
MASRLTLLTLLLLLLAGDRASSNPNATSSSSQDPESLQDRGEGKVATTVI
SKMLFVEPILEVSSLPTTNSTTNSATKITANTTDEPTTQPTTEPTTQPTI
QPTQPTTQLPTDSPTQPTTGSFCPGPVTLCSDLESHSTEAVLGDALVDFS
LKLYHAFSAMKKVETNMAFSPFSIASLLTQVLLGAGENTKTNLESILSYP
KDFTCVHQALKGFTTKGVTSVSQIFHSPDLAIRDTFVNASRTLYSSSPRV
LSNNSDANLELINTWVAKNTNNKISRLLDSLPSDTRLVLLNAIYLSAKWK
TTFDPKKTRMEPFHFKNSVIKVPMMNSKKYPVAHFIDQTLKAKVGQLQLS
HNLSLVILVPQNLKHRLEDMEQALSPSVFKAIMEKLEMSKFQPTLLTLPR
IKVTTSQDMLSIMEKLEFFDFSYDLNLCGLTEDPDLQVSAMQHQTVLELT
ETGVEAAAASAISVARTLLVFEVQQPFLFVLWDQQHKFPVFMGRVYDPRA

The invention claimed is:

1. A method for reducing antennary fucosylation of complex N-glycans in a glycoprotein that is recombinantly expressed in a human primary amniocyte cell line comprising at least one nucleic acid encoding gene products of the adenoviral E1 and pIX regions, comprising the step of overexpressing together with the glycoprotein a β-galactoside α-2,6-sialyltransferase 1 (ST6Gal1) and a β-galactoside α-2,3-sialyltransferase 4 (ST3Gal4).

2. The method of claim 1, wherein the glycoprotein is characterized by an at least 80% reduction in antennary fucosylation of complex N-glycans as compared to the same recombinant glycoprotein expressed without overexpression of the ST6Gal1 and the ST3Gal4.

3. The method of claim 1, wherein at least 80% of the complex N-glycan antennae of the recombinantly expressed glycoprotein are not fucosylated.

4. The method of claim 1, wherein the glycoprotein is selected from the group consisting of α1-antitrypsin (AAT), hepatocyte growth factor (HGF), Factor VII (FVII), Factor VIII (FVIII), Factor IX (FIX), von Willebrand-Factor (vWF), alkaline phosphatase, and C1 esterase inhibitor (C1-inhibitor; C1 Inh).

5. The method of claim 1, wherein the glycoprotein is a mammalian.

6. The method of claim 5, wherein the glycoprotein is a human glycoprotein.

7. The method of claim 1, further comprising
(i) a β-galactoside α-2,3-sialyltransferase 1 (ST3Gal1) wherein the ST3Gal1 is not overexpressed together with the glycoprotein, and/or
(ii) the expression of an α-1,3-mannosyl-glycoprotein 4-β-N-acetylglucosaminyltransferase A (GnTIVa), an α-1,3-mannosyl-glycoprotein 4-β-N-acetylglucosaminyltransferase B (GnTIVb), and an α-1,6-mannosylglycoprotein 6-β-N-acetylglucosaminyltransferase A (GnTV) are not reduced.

8. A cell line that is genetically modified to overexpress β-galactoside α-2,6-sialyltransferase 1 (ST6Gal1) and α-2,3-sialyltransferase 4 (ST3Gal4), and wherein the cell line is a human primary amniocyte cell line comprising at least one nucleic acid encoding the gene products of the adenoviral E1 and pIX regions.

9. The cell line of claim 8, wherein the cell line comprises endogenous gene(s) encoding the ST6Gal1 and the ST3Gal4, and further has at least one genetic element, selected from the group consisting of a promoter, an enhancing element, and a stabilizing element inserted into the genome in one or more position(s) suitable to cause overexpression of the ST6Gal1 and the ST3Gal4.

10. The cell line of claim 8, wherein the cell line comprises exogenous nucleic acid(s) encoding the ST6Gal1 and the ST3Gal4.

11. The cell line of claim 8, wherein the cell line is derived from a CAP cell line.

12. The cell line of claim 8, wherein the cell line is not genetically modified to
(i) overexpress a β-galactoside α-2,3-sialyltransferase 1 (ST3Gal1), and/or
(ii) reduce the expression of an α-1,3-mannosyl-glycoprotein 4-β-N-acetylglucosaminyltransferase A (GnTIVa), an α-1,3-mannosyl-glycoprotein 4-β-N-acetylglucosaminyltransferase B (GnTIVb), and an α-1,6-mannosylglycoprotein 6-β-N-acetylglucosaminyltransferase A (GnTV).

13. A recombinant glycoprotein having complex N-glycans, wherein antennary fucosylation of the complex N-glycans is reduced, so that at least 80% of the complex N-glycan antennae of the recombinant glycoprotein are not fucosylated, wherein said glycoprotein us is produced in a cell line according to claim 8.

14. The recombinant glycoprotein of claim 13, wherein the glycoprotein is selected from the group consisting of α1-antitrypsin (AAT), hepatocyte growth factor (HGF), Factor VII (FVII), Factor VIII (FVIII), Factor IX (FIX), von Willebrand-Factor (vWF), alkaline phosphatase, and C1 esterase inhibitor (C1-inhibitor; C1 Inh).

15. A method for the expression of a recombinant glycoprotein of claim 13, comprising the steps of:
   (a) providing a cell line that is genetically modified to overexpress a β-galactoside α-2,6-sialyltransferase 1 (ST6Gal1) and a α-2,3-sialyltransferase 4 (ST3Gal4), and wherein the cell line is a human primary amniocyte cell line comprising at least one nucleic acid encoding the gene products of the adenoviral E1 and pIX regions,
   (b) expressing the recombinant glycoprotein in said cell line, wherein the antennary fucosylation of the N-glycans of the glycoprotein is reduced; and
   (c) isolating the recombinant glycoprotein from the cells or the cell culture supernatant.

* * * * *

SEQUENCE LISTING

<160> NUMBER OF SEQ ID NOS: 4

<210> SEQ ID NO 1
<211> LENGTH: 333
<212> TYPE: PRT
<213> ORGANISM: Homo sapiens

<400> SEQUENCE: 1

Met Val Ser Lys Ser Arg Trp Lys Leu Leu Ala Met Leu Ala Leu Val
1               5                   10                  15

Leu Val Val Met Val Trp Tyr Ser Ile Ser Arg Glu Asp Arg Tyr Ile
            20                  25                  30

Glu Leu Phe Tyr Phe Pro Ile Pro Glu Lys Lys Glu Pro Cys Leu Gln
        35                  40                  45

Gly Glu Ala Glu Ser Lys Ala Ser Lys Leu Phe Gly Asn Tyr Ser Arg
    50                  55                  60

Asp Gln Pro Ile Phe Leu Arg Leu Glu Asp Tyr Phe Trp Val Lys Thr
65                  70                  75                  80

Pro Ser Ala Tyr Glu Leu Pro Tyr Gly Thr Lys Gly Ser Glu Asp Leu
                85                  90                  95

Leu Leu Arg Val Leu Ala Ile Thr Ser Ser Ile Pro Lys Asn Ile
            100                 105                 110

Gln Ser Leu Arg Cys Arg Arg Cys Val Val Gly Asn Gly His Arg
            115                 120                 125

Leu Arg Asn Ser Ser Leu Gly Asp Ala Ile Asn Lys Tyr Asp Val Val
    130                 135                 140

Ile Arg Leu Asn Asn Ala Pro Val Ala Gly Tyr Glu Gly Asp Val Gly
145                 150                 155                 160

Ser Lys Thr Thr Met Arg Leu Phe Tyr Pro Glu Ser Ala His Phe Asp
                165                 170                 175

Pro Lys Val Glu Asn Asn Pro Asp Thr Leu Leu Val Leu Val Ala Phe
            180                 185                 190

Lys Ala Met Asp Phe His Trp Ile Glu Thr Ile Leu Ser Asp Lys Lys
        195                 200                 205

Arg Val Arg Lys Gly Phe Trp Lys Gln Pro Pro Leu Ile Trp Asp Val
    210                 215                 220

Asn Pro Lys Gln Ile Arg Ile Leu Asn Pro Phe Phe Met Glu Ile Ala
225                 230                 235                 240

Ala Asp Lys Leu Leu Ser Leu Pro Met Gln Gln Pro Arg Lys Ile Lys
                245                 250                 255

Gln Lys Pro Thr Thr Gly Leu Leu Ala Ile Thr Leu Ala Leu His Leu
            260                 265                 270

Cys Asp Leu Val His Ile Ala Gly Phe Gly Tyr Pro Asp Ala Tyr Asn
        275                 280                 285

Lys Lys Gln Thr Ile His Tyr Tyr Glu Gln Ile Thr Leu Lys Ser Met
    290                 295                 300

Ala Gly Ser Gly His Asn Val Ser Gln Glu Ala Leu Ala Ile Lys Arg
305                 310                 315                 320

Met Leu Glu Met Gly Ala Ile Lys Asn Leu Thr Ser Phe
                325                 330

<210> SEQ ID NO 2
<211> LENGTH: 406
<212> TYPE: PRT
<213> ORGANISM: Homo sapiens

<400> SEQUENCE: 2

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
            20                  25                  30

Ser Tyr Tyr Asp Ser Phe Lys Leu Gln Thr Lys Glu Phe Gln Val Leu
            35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
            115                 120                 125

Pro Gly Pro Gly Ile Lys Phe Ser Ala Glu Ala Leu Arg Cys His Leu
            130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
    195                 200                 205

Leu Arg Phe Asn Gly Ala Pro Thr Ala Asn Phe Gln Gln Asp Val Gly
210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
            275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
            355                 360                 365

Tyr His Pro Leu Leu Tyr Glu Lys Asn Leu Val Lys His Leu Asn Gln
    370                 375                 380

Gly Thr Asp Glu Asp Ile Tyr Leu Leu Gly Lys Ala Thr Leu Pro Gly
385                 390                 395                 400

Phe Arg Thr Ile His Cys
                405
```

```
<210> SEQ ID NO 3
<211> LENGTH: 418
<212> TYPE: PRT
<213> ORGANISM: Homo sapiens

<400> SEQUENCE: 3

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380
```

-continued

```
Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
            405                 410                 415

Gln Lys

<210> SEQ ID NO 4
<211> LENGTH: 500
<212> TYPE: PRT
<213> ORGANISM: Homo sapiens

<400> SEQUENCE: 4

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335
```

```
Asp Gln Thr Leu Lys Ala Lys Val Gly Gln Leu Gln Leu Ser His Asn
            340             345             350

Leu Ser Leu Val Ile Leu Val Pro Gln Asn Leu Lys His Arg Leu Glu
        355             360             365

Asp Met Glu Gln Ala Leu Ser Pro Ser Val Phe Lys Ala Ile Met Glu
    370             375             380

Lys Leu Glu Met Ser Lys Phe Gln Pro Thr Leu Leu Thr Leu Pro Arg
385             390             395             400

Ile Lys Val Thr Thr Ser Gln Asp Met Leu Ser Ile Met Glu Lys Leu
                405             410             415

Glu Phe Phe Asp Phe Ser Tyr Asp Leu Asn Leu Cys Gly Leu Thr Glu
            420             425             430

Asp Pro Asp Leu Gln Val Ser Ala Met Gln His Gln Thr Val Leu Glu
        435             440             445

Leu Thr Glu Thr Gly Val Glu Ala Ala Ala Ala Ser Ala Ile Ser Val
    450             455             460

Ala Arg Thr Leu Leu Val Phe Glu Val Gln Gln Pro Phe Leu Phe Val
465             470             475             480

Leu Trp Asp Gln Gln His Lys Phe Pro Val Phe Met Gly Arg Val Tyr
            485             490             495

Asp Pro Arg Ala
            500
```